US00PP20586P2

(12) United States Plant Patent
Mehring-Lemper

(10) Patent No.: US PP20,586 P2
(45) Date of Patent: Dec. 15, 2009

(54) ***BEGONIA* PLANT NAMED 'BEGH 03897'**

(50) Latin Name: ***Begonia parvifolia*×*Begonia***
Varietal Denomination: BEGH 03897

(75) Inventor: Manfred Mehring-Lemper, Münden (DE)

(73) Assignee: Ernst Benary Samenzucht GmbH, Hann. Münden (DE)

( * ) Notice: Subject to any disclaimer, the term of this patent is extended or adjusted under 35 U.S.C. 154(b) by 0 days.

(21) Appl. No.: 12/284,877

(22) Filed: Sep. 22, 2008

(51) Int. Cl.
*A01H 5/00* (2006.01)

(52) U.S. Cl. ..... Plt./343

(58) Field of Classification Search ..... Plt./343
See application file for complete search history.

(56) References Cited

OTHER PUBLICATIONS

UPOV ROM GTITM Computer Database, GTI Jouve Retrieval Software 2008/06 Citation for 'BEGH 03897'.*

* cited by examiner

*Primary Examiner*—Wendy C Haas
(74) *Attorney, Agent, or Firm*—C. A. Whealy

(57) ABSTRACT

A new and distinct cultivar of *Begonia* plant named 'BEGH 03897', characterized by its compact and mounded plant habit; freely branching habit; dense and bushy growth habit; relatively small dark brown-colored leaves; and numerous sterile flowers that are pale pink in color.

1 Drawing Sheet

Botanical designation: *Begonia parvifolia*×*Begonia semperflorens.*

Cultivar denomination: 'BEGH 03897'.

BACKGROUND OF THE INVENTION

The present invention relates to a new and distinct cultivar of *Begonia* plant, botanically known as *Begonia parvifolia*× *Begonia semperflorens* and hereinafter referred to by the name 'BEGH 03897'.

The new *Begonia* plant is a product of a planned breeding program conducted by the Inventor in Hann. Münden, Germany. The objective of the breeding program was to develop new freely branching hybrid *Begonia* cultivars with attractive leaves and flowers.

The new *Begonia* plant originated from a cross-pollination made by the Inventor in 2003 of a proprietary selection of *Begonia parvifolia* identified as code number PAH 1/681, not patented, as the female, or seed, parent with a proprietary selection of *Begonia semperflorens* identified as code number GQ 1/495, not patented, as the male, or pollen, parent. The new *Begonia* was discovered and selected by the Inventor as a single plant from within the progeny of the stated cross-pollination in a controlled greenhouse environment in Hann. Münden, Germany in July, 2004.

Asexual reproduction of the new *Begonia* plant by terminal vegetative cuttings in a controlled greenhouse environment in Hann. Münden, Germany since February, 2005, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'BEGH 03897'. These characteristics in combination distinguish 'BEGH 03897' as a new and distinct cultivar of *Begonia:*

1. Compact and mounded plant habit.
2. Freely branching habit; dense and bushy growth habit.
3. Relatively small dark brown-colored leaves.
4. Numerous sterile flowers that are pale pink in color.

Plants of the new *Begonia* differ from plants of the female parent selection in the following characteristics:

1. Plants of the new *Begonia* are more mounded than and not as upright as plants of the female parent selection.
2. Leaves of plants of the new *Begonia* are smaller and darker in color than leaves of plants of the female parent selection.
3. Flowers of plants of the new *Begonia* are sterile whereas flowers of plants of the female parent selection are fertile.

Plants of the new *Begonia* differ from plants of the male parent selection in the following characteristics:

1. Plants of the new *Begonia* are more mounded than and not as upright as plants of the male parent selection.
2. Leaves of plants of the new *Begonia* are smaller than leaves of plants of the male parent selection.
3. Stems of plants of the new *Begonia* are red in color whereas stems of plants of the male parent selection are bronze in color.
4. Flowers of plants of the new *Begonia* are pale pink in color whereas flowers of plants of the male parent selection are red in color.
5. Flowers of plants of the new *Begonia* are sterile whereas flowers of plants of the male parent selection are fertile.

Plants of the new *Begonia* can also be compared to plants of the *Begonia* 'Cocktail Gin', not patented. In side-by-side comparisons conducted in Hann. Münden, Germany, plants of the new *Begonia* differed from plants of 'Cocktail Gin' in the following characteristics:

1. Plants of the new *Begonia* were larger and more vigorous than plants of 'Cocktail Gin'.
2. Flowers of plants of the new *Begonia* were sterile whereas flowers of plants of 'Cocktail Gin' were fertile.

BRIEF DESCRIPTION OF THE PHOTOGRAPHS

The accompanying colored photographs illustrate the overall appearance of the new *Begonia*, showing the colors as true as it is reasonably possible to obtain in colored reproductions of this type. Colors in the photographs may differ slightly from the color values cited in the detailed botanical description which accurately describe the colors of the new *Begonia* plant.

The photograph at the bottom of the sheet comprises a side perspective view of a typical flowering plant of 'BEGH 03897' grown in a container.

The photograph at the top of the sheet is a close-up view of typical flowers and leaves of 'BEGH 03897'.

DETAILED BOTANICAL DESCRIPTIONS

Plants used for the aforementioned photographs and following observations and measurements were grown in Loudon, N.H. in 10-cm containers and under commercial practice in a polyethylene-covered greenhouse during the spring. During the production of the plants, day temperatures ranged from 18° C. to 22° C. and night temperatures ranged from 16° C. to 18° C. Plants used for the photographs and the description were seven weeks from planting and were pinched one time. In the following description, color references are made to The Royal Horticultural Society Colour Chart, 2001 Edition, except where general terms of ordinary dictionary significance are used.

Botanical classification: *Begonia parvifolia*×*Begonia semperflorens* 'BEGH 03897'.

Parentage:

*Female, or seed, parent.*—Proprietary selection of *Begonia parvifolia* identified as code number PAH 1/681, not patented.

*Male, or pollen, parent.*—Proprietary selection of *Begonia semperflorens* identified as code number GQ 1/495, not patented.

Propagation:

*Type.*—By terminal vegetative cuttings.

*Time to initiate roots, summer.*—About 10 days at temperatures of about 20° C.

*Time to initiate roots, winter.*—About 14 days at temperatures of about 20° C.

*Time to produce a rooted young plant, summer.*—About three weeks at temperatures of about 20° C.

*Time to produce a rooted young plant, winter.*—About four weeks at temperatures of about 20° C.

*Root description.*—Fine, fibrous; white in color. Plants of the new *Begonia* have not been observed to form tubers.

*Rooting habit.*—Moderate branching; moderately dense.

Plant description:

*Plant form.*—Compact and mounded plant habit; freely branching with about five branches per plant; dense and bushy growth habit. Vigorous habit and moderate growth rate.

*Plant height.*—About 12 cm.

*Plant width.*—About 26 cm by 30 cm.

*Branch description.*—Length: About 20 cm. Diameter: About 6 mm. Internode length: About 3.8 cm. Texture: Smooth, glabrous. Color: Close to 199A.

*Leaf description.*—Arrangement: Simple, alternate. Length: About 8.7 cm. Width: About 7.2 cm. Shape: Roughly cordate to reniform. Apex: Acute. Base: Cordate. Margin: Irregularly crenate and sinuate; ciliate. Texture, upper and lower surfaces: Smooth, glabrous. Venation pattern: Palmate; reticulate. Color: Developing leaves, upper surface: Darker than 147A. Developing leaves, lower surface: Close to 177B. Fully expanded leaves, upper surface: Close to 200A; venation, close to N137A. Fully expanded leaves, lower surface: Close to 177A; venation, close to 146B. Petiole length: About 2 cm. Petiole diameter: About 3 mm. Petiole texture, upper and lower surfaces: Smooth, glabrous. Petiole color, upper and lower surfaces: Close to 146B.

Flower description:

*Flowering habit.*—Rounded flowers in axillary clusters of two to three. Freely flowering habit with about 22 flowers and flower buds per plant. Flowers outwardly drooping and arising from below the foliage.

*Fragrance.*—None detected.

*Natural flowering season.*—Plants flower continuously during the spring in Germany. Flowers last about four to five days on the plant; flowers not persistent.

*Flowers size.*—Diameter: About 1.5 cm by 1.8 cm. Depth (height): About 1.5 cm.

*Flower buds.*—Shape: Flattened oval. Length: About 1 cm. Diameter: About 8 mm. Color: Close to N155D.

*Tepals.*—Arrangement: Rosette. Quantity per flower: Usually about six per flower arranged in a one to two whorls. Length: About 1 cm. Width: About 7 mm. Shape: Obovate. Apex: Rounded, obtuse. Base: Acute. Margin: Entire. Texture, upper and lower surfaces: Smooth, glabrous; velvety. Color: When opening, upper surface: Close to 69C. When opening, lower surface: Close to 69D. Fully opened, upper surface: Close to 65B to 65C; color does not fade with development. Fully opened, lower surface: Close to 65D; color does not fade with development.

*Flower bracts.*—Quantity/arrangement: Three in a single whorl. Length: About 5 mm. Diameter: About 5 mm. Shape: Ovate. Apex: Erose. Base: Acute. Margin: Entire. Texture, upper and lower surfaces: Smooth, glabrous. Color, upper surface: Close to 159C. Color, lower surface: Close to 159D.

*Peduncles.*—Angle: About 45° from the stem axis. Length: About 8 mm. Diameter: About 1 mm. Texture: Smooth, glabrous. Color: Close to N170D.

*Reproductive organs.*—Stamens: None observed. Pistils: Pistil length: About 1.3 cm. Style length: About 1 mm. Style color: Close to 145C. Stigma color: Close to 153C. Ovary color: Close to 193C.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 5° C. to about 35° C.

It is claimed:

1. A new and distinct *Begonia* plant named 'BEGH 03897' as illustrated and described.

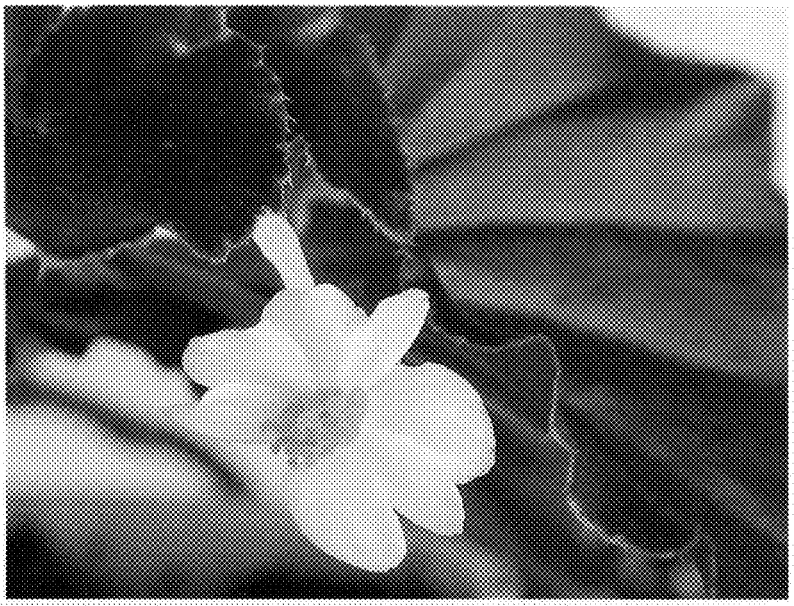
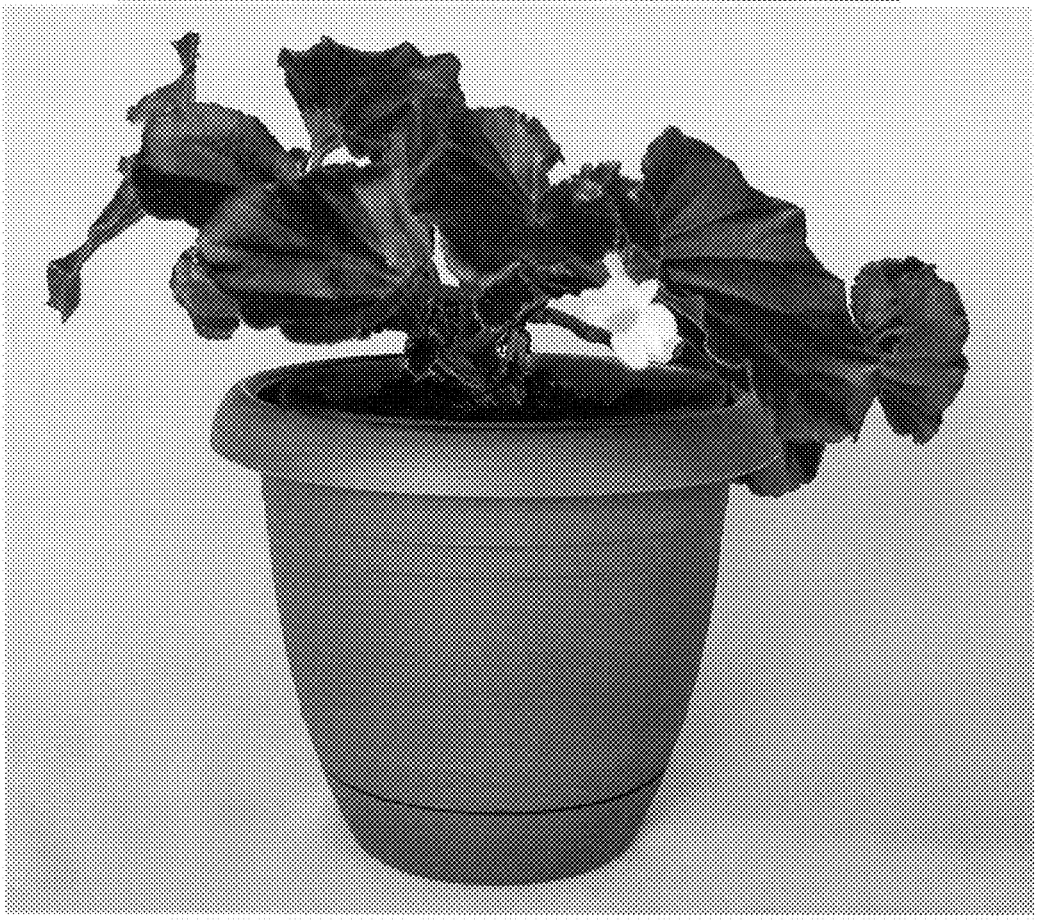

* * * * *